United States Patent [19]
Segawa et al.

[11] Patent Number: 5,993,794
[45] Date of Patent: Nov. 30, 1999

[54] PERMING AGENT AND METHOD OF TREATING HAIR WITH THE SAME

[75] Inventors: Hirotsugu Segawa; Yuichi Ayano, both of Osaka, Japan

[73] Assignee: Takara Belmont Kabushiki Kaisha, Osaka, Japan

[21] Appl. No.: 08/977,737

[22] Filed: Nov. 25, 1997

[30] Foreign Application Priority Data

Feb. 21, 1997 [JP] Japan .................................... 9-037448

[51] Int. Cl.⁶ ....................................................... A61K 7/09
[52] U.S. Cl. ...................... 424/70.51; 424/70.5; 424/70.2
[58] Field of Search .................................. 424/70.2–70.5; 427/70.51, 70.5, 70.2

[56] References Cited

U.S. PATENT DOCUMENTS

| | | | |
|---|---|---|---|
| 4,913,900 | 4/1990 | Kolc ............................................ | 424/72 |
| 5,154,918 | 10/1992 | Maignan ..................................... | 424/72 |
| 5,277,206 | 1/1994 | Rose et al. ............................... | 132/204 |
| 5,637,295 | 6/1997 | Lang ........................................ | 424/70.2 |

FOREIGN PATENT DOCUMENTS

000286774A1  10/1988  European Pat. Off. .

*Primary Examiner*—Thurman K. Page
*Assistant Examiner*—Todd D Ware
*Attorney, Agent, or Firm*—Nikaido Marmelstein Murray & Oram LLP

[57] ABSTRACT

The present invention provides improved perming agents and perming methods which can minimize damage to hair and simplify perming processes simultaneously and also can relieve a pain of a subject to be permed by shortening time required for a perming operation. The present invention uses a perming agent containing 2–7% of one kind or more than two kinds of mercaptan selected from thioglycolic acid, salt of thioglycolic acid, cysteine and acetyl cysteine and 1.5–17.5% of one or more than two kinds of disulfide selected from dithiodiglycolic acid, salt of dithiodiglycolic acid and cysteine, with a mixing ratio of disulfide to mercaptan being 0.75–2.5 to induce simultaneous progression of oxidation and reduction and, when necessary, in combination with a second agent containing an oxidizing agent for giving permanent wave to hair or curing wavy hair.

5 Claims, No Drawings

PERMING AGENT AND METHOD OF TREATING HAIR WITH THE SAME

FIELD OF THE INVENTION

The present invention relates to a perming agent and a method of treating hair with the same, more particularly, to a simultaneous oxidizing and reducing type perming agent for giving permanent wave to hair or curing wavy hair (hereinafter referred to as "perming") which can prevent the hair from damage and shorten a time required to treat the hair.

DESCRIPTION OF THE PRIOR ART

In a conventional method of treating hair through a perming operation, the hair is wound around rods while applying a first agent which contains reducing agents, such as thioglycolic acid, salt of thioglycolic acid, cysteine and the like, as its principal agent, and adjusted to be less than pH 9.6 or to an alkaline condition by adding an alkaline agent such as ammonia, monoethanolamine, ammonium bicarbonate and the like. It is made certain by means of a test curling that the hair is plasticized enough after the wound hair being left for 10–15 minutes, and then the first agent is completely washed off from the hair with water as an intermediate process. Then a second agent containing an oxidizing agent such as bromate or hydrogen peroxide is applied to the hair wound around the rods and then the rods are removed from the hair after clasping 10–15 minutes, and the second agent is washed off from the hair with water.

However, in such conventional method, since at least 1–3 minutes of intermediate washing time is necessary to remove the first agent from hair wound around the rods, the hair is swelled and peptide contained in the hair is flown out from the hair through interstices of expanded cuticles thereof. As a result, It has been one of the reasons to damage the hair. In addition, a person subjected to be permed feels a significant pain as he or she has to stay at a hair wash stand another 10–15 extra minutes following the application of the second agent to hair after the intermediate washing.

A single-bath perming agent requiring no second agent has been proposed. However, when this type of a perming agent is utilized, after treating with a first agent, the hair must be washed off, as an intermediary process, with water to completely remove the first agent from the hair as being wound around the rods and then left as is for 15–20 minutes to be oxidized by air. Therefore, the problems encountered with the two bath perming agent employing the second agent are not only unsolved even in the single bath process but it causes another defect such that insufficient oxidation may cause serious damage to the hair.

PROBLEMS TO BE SOLVED BY THE INVENTION

It is therefore an object of the present invention to overcome defects encountered with the conventional two bath or single-bath perming agents and to provide an improved perming agent and a method of treating hair by utilizing the same wherein a process of perming operation is simplified, the hair is prevented from damage and a time required for a perming operation is shortened, thus giving a person relief from pain during a perming treatment of the hair.

MEANS OF SOLVING THE PROBLEM

The above objective of the present invention is achieved by using a simultaneous oxidizing and reducing type perming agent comprising, in combination, a first agent for giving a permanent wave to hair or for curing wavy hair, which contains 2–7% of one kind or two or more than two kinds of mercaptan selected from thioglycolic acid, salt of thioglycolic acid, cysteine and acetyl cysteine, and 1.5–17.5% of one kind or two or more than two kinds of disulfide selected from dithiodiglycolic acid, salt of dithiodiglycolic acid and cystine, wherein a mixing ratio of disulfide to mercaptan is 0.75–2.5, and a second agent containing an oxidizing agent for a permanent wave of hair or correction of wavy hair.

Another object of the present invention is to provide a method of perming hair wherein winding hair around rods by applying, to the hair, a first agent for giving a permanent wave to hair or for curing wavy hair containing 1–5% of one or more kinds of mercaptan selected from thioglycolic acid and salt of thioglycolic acid, 1–2% of one or more kinds of mercaptan selected from cysteine and acetyl cysteine, 1.5–17.5% of one kind or two or more than two kinds of disulfide selected from dithiodiglycolic acid, salt of dithiodiglycolic acid and cystine, wherein a mixing ratio of disulfide to mercaptan is 0.75–2.5, washing off the first agent from the hair after elapsing a predetermined time, removing the rods from the hair immediately after the washing off, applying to the hair a second agent containing hydrogen peroxide for giving a permanent wave or for curing wavy hair to the extent that the second agent permeates throughout the hair, and washing off the second agent from the hair immediately after the permeation of the second agent throughout the hair, whereby more preferable results are obtained.

Yet another object of the present invention is to provide a method of giving a permanent wave to hair or curing wavy hair wherein winding hair around rods by applying to the hair a perming agent of giving a permanent wave to hair or curing wavy hair containing at or less than 1% of mercaptan selected from thioglycolic acid and salt of thioglycolic acid, 2–7% of one or more kinds of mercaptan selected from cysteine and acetyl cysteine, 1.5–17.5% of one kind or two or more than two kinds of disulfide selected from dithiodiglycolic acid, salt of dithiodiglycolic acid and cystine, wherein a mixing ratio of disulfide to mercaptan is 0.75–2.5, washing off the perming agent from the hair after elapsing a predetermined time, and removing the rods from the hair immediately after said washing off, whereby preferable results are obtained even though the second perming process is eliminated.

EMBODIMENTS

In accordance with he present invention, mercaptan which is used as a first agent for giving a permanent wave to hair consists of one kind or two or more than two kinds of mercaptan selected from thioglycolic acid, salt of thioglycolic acid, cysteine and acetyl cysteine, however, said salt of thioglycolic acid can be ammonia thioglycolic acid, sodium thioglycolic acid, potassium thioglycolic acid, monoethanolamine thioglycolic acid, triethanolamine thioglycolic acid and the like. A mixing rate of such mercaptan is preferably within a range of 2–7%. If it is less than 2%, a sufficient power to give a permanent wave to the hair cannot be obtained. If it is more than 7% there is caused a serious damage to the hair.

In accordance with the present invention, more preferable results can be expected when the first agent for giving a permanent wave to hair comprises 1–5% of one or more kinds of mercaptan selected from thioglycolic acid and salt of thioglycolic acid and 1–2% of one or more kinds of mercaptan selected from cysteine and acetyl cysteine.

Furthermore, in accordance with the present invention, even if the use of any second agent is omitted, preferable effects can also be obtained when the first agent for giving a permanent wave to hair comprises less than 1% of one or more kinds of mercaptan selected from thioglycolic acid and salt of thioglycolic acid and 2–7% of one or more kinds of mercaptan selected from cysteine and acetyl cysteine.

In accordance with the present invention, disulfide to be used as the first agent for the permanent wave consists of one kind or two or more than two kinds of disulfide selected from dithiodiglycolic acid, salt of dithiodiglycolic acid and cystine, however, said salt of dithiodiglycolic acid can be ammonia dithiodiglycolic acid, sodium dithiodiglycolic acid, potassium dithiodiglycolic acid, monoethanolamine dithiodiglycolic acid, triethanolamine dithiodiglycolic acid and the like. The mixing rate of such disulfide is preferably within a range of 1.5–17.5%. The mixing ratio of disulfide to mercaptan is preferably within a range of 0.75–2.5. If the mixing ratio of disulfide to mercaptan is less than 0.75, the act of oxidation is insufficient and if it is more than 2.5, the act of reduction is insufficient. In both cases, an adequate wave cannot be given to the hair.

An oxidizing agent to be used as the second permanent wave agent of the present invention can be hydrogen peroxide, sodium bromate, potassium bromate and the like. The oxidizing agent preferably contains 1–3% of hydrogen peroxide. If a blended amount of hydrogen peroxide in the second agent is less than 1%, its oxidizing power is insufficient and if it is more than 3%, there is caused considerable damage to the hair.

According to the present invention, the first and second permanent wave agents, within the allowable extent of effects of the present invention, can include high or low molecular surface active agent such as a cationic, anionic, amphoteric and nonionic, or other components such as urea, higher alcohol, hydrolysate of protein, amino acid, hair growth agent, acid dye, perfume as an additive or compounding agent.

An act of mechanism of the conventional perming agent is that twenty percent (20%) of cystine combination contained in hair is reduced by the first agent which contains a reducing agent such as thioglycolic acid (10–15 minutes after the first agent being applied, then adequate plasticity of the hair is confirmed by test curling) and the reduced cystine combination is recombined and a state of curled hair is fixed by the next process wherein the first agent is washed off from the hair wound around the rods with water through an intermediate washing process, then the second agent containing an oxidizing agent is applied to the hair wound around the rods, and allowed to elapse for 10–15 minutes.

On the other hand, according to the present invention, if a rate of mixing of mercaptan such as thioglycolic acid to disulfide such as dithiodiglycolic acid exceeds 0.75, oxidation and reduction take place simultaneously and reach to a state of equilibrium by approximately 20 minutes after. At this time, there is left approximately five percent (5%) of cystine combination as being reduced, however, a formed wave can be fully maintained even if the hair is removed from the rods, whereas no plasticity remains as in the hair treated by a conventional first agent. However, if the process in perming is terminated at this stage, in some cases, the waves of the hair may come out in about one week or so, thus the second agent containing an oxidizing agent is applied to the hair after being removed from the rods in order to stop the action of the residual first agent and to obtain a long durable hair wave.

Therefore, according to the present invention, since the oxidation and reduction progress essentially by the first agent only, intermediate washing off with water which has been required in the conventional perming method is not necessarily required or, even if the washing off is implemented, it is enough to remove chemical agents left on the surface of the hair through a simple and short process, as a result, preventing peptide of the hair from flowing out with water as well as the hair from being damaged. Further, the application of the second agent of the present invention is not essential to the reaction of oxidation and reduction induced by the first agent and is used merely as a supplementary process and, therefore, the second agent can be washed off immediately after being reached to the whole hair just like use of a rinse. Thus, in accordance with the present invention, there is provided a simple perming operation within a short period of time.

The present invention will now be described more in detail with reference to examples, however, should not be construed as limited to only the examples set forth herein.

EXAMPLE 1

Permanent wave first agents A–C (products of the present invention), D and F (products for comparison), and second agents F and G are prepared in accordance with prescription shown in Tables 1–7. By using these agents, tests for wave effectiveness rate, reduction rate measurement, wave keeping rate and hair strength were carried out. The results are shown in Tables 8 and 9.

TABLE 1

Permanent wave first agent A
(Prescription 1: the present invention)

| | |
|---|---|
| Solution of ammonia thioglycolic acid (containing 50% of thioglycolic acid) | 6.0 g |
| Solution of ammonia dithiodiglycolic acid (containing of 40% of dithiodiglycolic acid) | 10.0 g |
| Ammonia water (25%) (adjusted to pH 9) | Adequate amount |
| Polydimethylmetylene piperidinium chloride | 0.4 g |
| Emulsifier | 3.0 g |
| Purified water to adjust the total amount to 100 ml | Adequate amount |

TABLE 2

Permanent wave first agent B
(Prescription 2: the present invention)

| | |
|---|---|
| Solution of ammonia thioglycolic acid (containing 50% of thioglycolic acid) | 6.0 g |
| Cysteine hydrochloride | 1.5 g |
| Solution of ammonia dithiodiglycolic acid (containing 40% of dithiodiglycolic acid) | 10.0 g |
| Ammonia water (25%) (adjusted to pH 9) | Adequate amount |
| Polydimethylmetylene piperidinium chloride | 0.4 g |
| Emulsifier | 3.0 g |
| Purified water to adjust the total amount to 100 ml | Adequate amount |

TABLE 3

Permanent wave first agent C
(Prescription 3: the present invention)

| | |
|---|---|
| Solution of monoethanolamine thioglycolic acid (containing 50% of thioglycolic acid) | 6.0 g |
| Cysteine hydrochloride | 7.3 g |
| Solution of ammonia dithiodiglycolic acid (containing 40% of dithiodiglycolic acid) | 20.0 g |
| Ammonia water (25%) (adjusted to pH 7.9) | Adequate amount |

TABLE 3-continued

Permanent wave first agent C
(Prescription 3: the present invention)

| | |
|---|---|
| Ammonium bicarbonate | 3.0 g |
| Polydimethylmetylene piperidinium chloride | 0.4 g |
| Emulsifier | 3.0 g |
| Purified water to adjust the total amount to 100 ml | Adequate amount |

TABLE 4

Permanent wave first agent D
(Prescription 4: comparison)

| | |
|---|---|
| Solution of ammonia thioglycolic acid (containing 50% of thioglycolic acid) | 8.0 g |
| Ammonia water (25%) (adjusted to pH 9) | Adequate amount |
| Polydimethylmetylene piperidinium chloride | 0.4 g |
| Emulsifier | 3.0 g |
| Purified water to adjust the total amount to 100 ml | Adequate amount |

TABLE 5

Permanent wave first agent E
(Prescription 5: comparison)

| | |
|---|---|
| Solution of ammonia thioglycolic acid (containing 50% of thioglycolic acid) | 13.6 g |
| Solution of ammonia dithiodiglycolic acid (containing 40% of dithiodiglycolic acid) | 2.0 g |
| Ammonia water (25%) (adjusted to pH 8.1) | Adequate amount |
| Ammonium bicarbonate | 4.0 g |
| Polydimethylmetylene piperidinium chloride | 0.4 g |
| Emulsifier | 3.0 g |
| Purified water to adjust the total amount to 100 ml | Adequate amount |

TABLE 6

Permanent wave second agent F
(Prescription 6)

| | |
|---|---|
| Sodium bromate | 7.0 g |
| Polyoxythelenelauryl sulfate | 1.0 g |
| Purified water to total up the amount to 100 ml | Adequate amount |

TABLE 7

Permanent wave second agent G
(Prescription 7)

| | |
|---|---|
| Hydrogen peroxide (35%) | 6.6 g |
| Sodium pyrophosphate | 0.2 g |
| Phosphoric acid to adjust the pH to 3.0 | Adequate amount |
| Lauryldimethylamine betaine acetate | 1.0 g |
| Purified water to adjust the total amount to 100 ml | Adequate amount |

Wave Effectiveness Rate Test

Twenty-five (25) pieces of hair were wound around the Curvy-type waving device and soaked in the first agent for 1 minute and transferred into an empty container and sealed, and then the container was placed in a thermostat at 40° C. The waving device with hair wound therearound was taken out after a lapse of specified period of time and washed off with water, soaked in the second agent for a specified period of time and then washed off with water. After such treatment, the hair was removed from the waving device to determine the wave effectiveness rate.

Reduction Rate Measurement Test

The hair treated with the first agent in the wave effectiveness rate test is washed with 0.5% aqueous solution of sodium sulfite, further soaked in 0.5% aqueous solution of sodium sulfite for 30 minutes and that in 1% aqueous solution of iodine sodium acetate, heated in a hot water bath for one hour, washed off with water and dried. The hair was hydrolyzed by using hydrochloric acid and then an amino acid analysis was performed to calculate a reduction rate from the amount of cystine contained in the hair before the treatment with the first agent and from the amount of carboxymethylcysteine contained in the hair after treatment with the first agent.

Wave Keeping Rate Test

The hair, the wave effectiveness rate of which was already measured by the wave effectiveness test, was suspended indoors by applying a load of 7.6 g imposed thereon and, after a week, its effectiveness rate was measured and then a wave keeping rate was calculated provided that the wave effectiveness rate obtained immediately after the perming treatment is set to 100.

Hair Strength Test

Twenty pieces of hair having approximately 20 cm in length were tied with a metal fitting at the center thereof and cut at the center to make two bundles of hair. One of the two bundles of hair was soaked in the first agent for 1 minute, then taken out the first agent and transferred into an empty container and sealed. The container containing the hair was left in a thermostat at 40° C. The hair was taken out of the container after a lapse of a specified period of time and washed off with water, and then were soaked in the second agent for a predetermined period of time and washed off with water after being taken out of the second agent. After drying naturally, a breakdown load of the hair was measured by using a tension tester (Toyo Boldwin, Tensiron UMT-2-5HR). Then, a relative value was calculated in consideration of a breakdown load of untreated hair being set to 100 and thus measured value was used as the strength of hair.

TABLE 8

| Test Number | 1 | 2 | 3* | 4* | 5 |
|---|---|---|---|---|---|
| First agent | A | A | D* | D* | C |
| Lapse time (Min) | 10 | 20 | 10 | 20 | 20 |
| Second agent | F | F | F | F | — |
| Lapse time (Min) | 5 | 5 | 15 | 15 | — |
| Reduction rate (%) | 7.0 | 4.3 | 14.5 | 18.6 | |
| Wave effective rate (%) | 35 | 47 | 34 | 48 | 45 |
| Wave maintaining rate (%) | | 78 | | 62 | 78 |

*Comparison example

Table 8 shows that, though the perming first agent A of the present invention presents less than half of the reduction rate compared with that of the conventional first perming agent D, it has the effectiveness rate being equivalent to that of the first agent D. This means that oxidation and reduction progress in parallel. Moreover, the conventional perming second agent requires about 15 minutes to wait for perming. However, the second agent of the present invention requires only about one third of that of the conventional one and, with this, it gives a sufficient wave maintaining rate for the hair. In addition, the first perming agent C of the present invention successfully form a firm wave and have a sufficient wave maintaining rate even if the use of the second agent is omitted.

TABLE 9

| Test Number | 6 | 7 | 8* |
|---|---|---|---|
| First agent | A | B | E* |
| Lapse time (Min.) | 15 | 15 | 15 |
| Second agent | F | G | F |
| Lapse time (Min.) | 5 | 1 | 10 |
| Wave effective rate (%) | 44 | 45 | 43 |
| Hair strength rate (%) | 98 | 101 | 89 |

*Comparison example

From Table 9, it is to be understood that there is no decrease in strength of hair according to the perming method of the present invention as compared with that of the conventional method.

EXAMPLE 2

By using the first agent H and second agent I (products of the present invention) for giving permanent wave to hair in accordance with the prescription shown in Tables 10 and 11, perming treatment was carried out in the way as described below. First, the hair was wound around the rods while applying the perming first agent to hair, and the hair wound around the rods was heated by a heater at a temperature of less than 50° C., it was left for about 20 minutes. Immediately after elapsing this time, the first agent H was washed off from the hair, and the hair was removed from the rods. Next, the perming second agent I was applied to hair and one minute later, it was washed off from the hair with water. As a result, even though the hair was removed from the rods before the treatment of the second agent and the time given to the treatment of the second agent was as short as one minute, an elastic and firm wave was given to the hair and, even one week later, there was no noticeable wave down on the treated hair.

TABLE 10

Permanent wave first agent H
(Prescription 8: the present invention)

| | |
|---|---|
| Solution of ammonia thioglycolic acid | 8.0 g |
| (containing 50% of thioglycolic acid) | |
| Cysteine hydrochloride | 1.5 g |
| Acetylcysteine | 0.5 g |
| Cystine | 0.2 g |
| Solution of ammonia dithiodiglycolic acid | 20.0 g |
| (containing 40% of dithiodiglycolic acid) | |
| Ammonia water (25%) | Adequate amount |
| (adjusted to pH 8.5) | |
| Ammonium bicarbonate | 1.0 g |
| Polydimethylmetylene piperidinium chloride | 0.8 g |
| Emulsifier | 20.0 g |
| Purified water to adjust the total amount to 100 ml | Adequate amount |

TABLE 11

Permanent wave second agent I
(Prescription 9)

| | |
|---|---|
| Hydrogen peroxide (35%) | 6.6 g |
| Sodium pyrophosphate | 0.2 g |
| Phosphoric acid to adjust the pH to 3.0 | Adequate amount |
| Emulsifier | 20.0 g |
| Purified water to adjust the total amount to 100 ml | Adequate amount |

EXAMPLE 3

Using a single-bath type wavy hair curing agent J prepared in accordance with the prescription shown in Table 12, following straightening treatment was carried out. That is, the wavy hair curing agent J was applied to wavy hair and, while the hair was being extended by a wide-tooth comb, it was left for about 20 minutes and then washed off with water. As a result, the wavy hair were cured without giving damage to the hair, thus glossy straight hair was achieved and no return to the wavy hair was observed even one week later.

TABLE 12

Single-bath type wavy hair correction agent J
(Prescription 10)

| | |
|---|---|
| Cysteine hydrochloride | 7.3 g |
| Solution of monoethanolamine thioglycolic acid | 1.0 g |
| (containing 50% of thioglycolic acid) | |
| Solution of ammonia dithiodiglycolic acid | 10.0 g |
| (containing 40% of dithiodiglycolic acid) | |
| Ammonia water (25%) | Adequate amount |
| (adjusted to pH 7.9) | |
| Ammonium bicarbonate | 3.0 g |
| Emulsifier | 20.0 g |
| Purified water to adjust the total amount to 100 ml | Adequate amount |

Effects of the Invention

The present invention allows a powerful perming which can minimize damage to hair. It also permits the omission of the test curling, intermediate washing process and the use of the second agent and has the simultaneous effect of shortening time required for perming operation and of simplifying perming processes thereof.

What is claimed is:

1. A simultaneous oxidizing and reducing perming agent comprising, in combination:
   a first agent for giving permanent wave to hair or curing wavy hair, which contains 2–7% of at least one mercaptan selected from the group consisting of thioglycolic acid, salt of thioglycolic acid, cysteine and acetyl cysteine, and 1.5–17.5% of at least one disulfide selected from the group consisting of dithiodiglycolic acid, salt of dithiodiglycolic acid and cystine, wherein a mixing ratio of disulfide to mercaptan is 0.75–2.5; and
   a second agent containing an oxidizing agent for giving permanent wave to hair or curing wavy hair.

2. A simultaneous oxidizing and reducing perming agent comprising, in combination:
   a first agent for giving permanent wave to hair or curing wavy hair, which contains 1–5% of at least one mercaptan selected from the group consisting of thioglycolic acid and salt of thioglycolic acid, 1–2% of at least one mercaptan selected from the group consisting of cysteine and acetyl cysteine, and 1.5–17.5% of at least one disulfide selected from the group consisting of dithiodiglycolic acid, salt of dithiodiglycolic acid and cystine, wherein a mixing ratio of disulfide to mercaptan is 0.75–2.5; and
   a second agent containing hydrogen peroxide for giving permanent wave to hair or curing wavy hair.

3. A simultaneous oxidizing and reducing perming agent of single-bath type for giving permanent wave to hair or curing wavy hair comprising:
   an agent containing less than 1% of at least one mercaptan selected from the group consisting of thioglycolic acid and salt of thioglycolic acid, 2–7% of at least one mercaptan selected from the group consisting of cysteine and acetyl cysteine, 1.5–17.5% of at least one disulfide selected from the group consisting of dithiodiglycolic acid, salt of dithiodiglycolic acid and cystine, wherein a mixing ratio of disulfide to mercaptan is 0.75–2.5.

4. A method of perming hair comprising the steps of:

winding hair around rods by applying a first agent for giving permanent wave to hair or curing wavy hair containing 1–5% of at least one mercaptan selected from the group consisting of thioglycolic acid and salt of thioglycolic acid, 1–2% of at least one mercaptan selected from the group consisting of cysteine and acetyl cysteine, and 1.5–17.5% of at least one disulfide selected from the group consisting of dithiodiglycolic acid, salt of dithiodiglycolic acid and cystine, wherein a mixing ratio of disulfide to mercaptan is 0.75–2.5;

washing off the first agent from the hair after elapsing a predetermined time;

removing the rods from the hair immediately after said washing off;

applying a second agent, which contains hydrogen peroxide for giving permanent wave to hair or curing wavy hair, to the hair to such an extent that the second agent permeates throughout the hair; and washing off the second agent from the hair immediately after the permeation of the second agent throughout the hair.

5. A method of perming hair comprising the steps of:

winding hair around rods by applying a perming agent for giving permanent wave to hair or curing wavy hair containing less than 1% of mercaptan selected from the group consisting of thioglycolic acid and salt of thioglycolic acid, 2–7% of at least one mercaptan selected from the group consisting of cysteine and acetyl cysteine, 1.5–17.5% of at least one disulfide selected from the group consisting of dithiodiglycolic acid, salt of dithiodiglycolic acid and cystine, wherein a mixing ratio of disulfide to mercaptan is 0.75–2.5;

washing off the perming agent from the hair after elapsing a predetermined time; and removing the rods from the hair immediately after said washing off.

* * * * *